United States Patent
Assell et al.

(10) Patent No.: US 8,900,279 B2
(45) Date of Patent: Dec. 2, 2014

(54) BONE SCREW

(75) Inventors: Robert L. Assell, St. Paul, MN (US);
Brian P. Beaubien, St. Paul, MN (US);
Jeremy Thomas Carr, Lauderdale, MN (US)

(73) Assignee: Zyga Technology, Inc., Minnetonka, MN (US)

( * ) Notice: Subject to any disclaimer, the term of this patent is extended or adjusted under 35 U.S.C. 154(b) by 325 days.

(21) Appl. No.: 13/493,186

(22) Filed: Jun. 11, 2012

(65) Prior Publication Data
US 2012/0323285 A1 Dec. 20, 2012

Related U.S. Application Data

(60) Provisional application No. 61/495,212, filed on Jun. 9, 2011.

(51) Int. Cl.
*A61B 17/04* (2006.01)
*A61B 17/86* (2006.01)
*A61F 2/08* (2006.01)
*A61B 17/88* (2006.01)

(52) U.S. Cl.
CPC ........... *A61B 17/869* (2013.01); *A61B 17/8625* (2013.01); *A61B 17/8875* (2013.01); *A61B 17/866* (2013.01)
USPC ........................................................ 606/304

(58) Field of Classification Search
CPC .................................................... A61B 17/869
USPC ....................................................... 606/304
See application file for complete search history.

(56) References Cited

U.S. PATENT DOCUMENTS

| 5,242,444 | A | 9/1993 | MacMillan |
| 5,334,205 | A | 8/1994 | Cain |
| 5,928,239 | A | 7/1999 | Mirza |
| 6,358,251 | B1 | 3/2002 | Mirza |
| 6,440,138 | B1 | 8/2002 | Reiley et al. |
| 6,635,059 | B2 | 10/2003 | Randall et al. |

(Continued)

FOREIGN PATENT DOCUMENTS

| DE | 202009006906 U1 | 7/2009 |
| EP | 0 369 603 A1 | 5/1990 |

(Continued)

OTHER PUBLICATIONS

Notification of Transmittal of the International Search Report and the Written Opinion of the International Searching Authority, or the Declaration (PCT/US2012/041912) dated Nov. 2, 2012 (16 pages).

*Primary Examiner* — Sameh Boles
(74) *Attorney, Agent, or Firm* — Dicke, Billig & Czaja, PLLC (57) ABSTRACT

A bone screw including a main body portion having a proximal end and a distal end. An external threaded surface and an internal threaded surface are formed on the main body portion. The external threaded surface intersects the internal threaded surface proximate a lower surface of the external threaded surface and a lower surface of the internal threaded surface. A plurality of bone growth apertures is defined on the surface of the main body portion where the external threaded surface and the internal threaded surface are not located. The bone growth apertures comprise between about 10 percent and about 60 percent of the surface of the main body portion.

7 Claims, 4 Drawing Sheets

(56) References Cited

U.S. PATENT DOCUMENTS

| | | |
|---|---|---|
| 6,679,886 B2 | 1/2004 | Weikel et al. |
| 6,726,690 B2 | 4/2004 | Eckman |
| 6,740,090 B1 | 5/2004 | Cragg et al. |
| 6,746,451 B2 | 6/2004 | Middleton et al. |
| 6,821,276 B2 | 11/2004 | Lambrecht |
| 6,923,813 B2 | 8/2005 | Phillips et al. |
| 6,939,351 B2 | 9/2005 | Eckman |
| D601,711 S | 10/2009 | Lin |
| 7,699,849 B2 | 4/2010 | Eckman |
| 7,867,233 B2 | 1/2011 | Shaolian et al. |
| 7,879,038 B2 | 2/2011 | Reiley et al. |
| 7,909,827 B2 | 3/2011 | Reiley et al. |
| 7,914,545 B2 | 3/2011 | Ek |
| 8,109,957 B2 | 2/2012 | Stad et al. |
| 8,114,084 B2 | 2/2012 | Betts |
| 8,348,950 B2 | 1/2013 | Assell et al. |
| 2001/0049527 A1 | 12/2001 | Cragg |
| 2003/0191474 A1 | 10/2003 | Cragg et al. |
| 2004/0267269 A1 | 12/2004 | Middleton et al. |
| 2005/0137600 A1 | 6/2005 | Jacobs et al. |
| 2005/0159746 A1 | 7/2005 | Grob et al. |
| 2005/0267482 A1 | 12/2005 | Hyde, Jr. |
| 2006/0111780 A1 | 5/2006 | Petersen |
| 2006/0155289 A1 | 7/2006 | Windhager et al. |
| 2007/0123889 A1 | 5/2007 | Malandain et al. |
| 2007/0198020 A1 | 8/2007 | Reiley et al. |
| 2007/0260270 A1 | 11/2007 | Assell |
| 2008/0009861 A1 | 1/2008 | Stark |
| 2008/0009875 A1 | 1/2008 | Sankaran et al. |
| 2008/0091199 A1 | 4/2008 | Cragg |
| 2008/0114364 A1 | 5/2008 | Goldin et al. |
| 2008/0269754 A1 | 10/2008 | Lutz |
| 2008/0294167 A1 | 11/2008 | Schumacher et al. |
| 2009/0138053 A1 | 5/2009 | Assell et al. |
| 2009/0216238 A1 | 8/2009 | Stark |
| 2009/0259261 A1 | 10/2009 | Reiley |
| 2009/0319043 A1 * | 12/2009 | McDevitt et al. .......... 623/13.14 |
| 2010/0030216 A1 | 2/2010 | Arcenio |
| 2010/0131011 A1 | 5/2010 | Stark |
| 2010/0241123 A1 | 9/2010 | Middleton et al. |
| 2011/0028978 A1 | 2/2011 | Li et al. |
| 2011/0087294 A1 | 4/2011 | Reiley |
| 2011/0098709 A1 | 4/2011 | Malandain et al. |
| 2011/0118796 A1 | 5/2011 | Reiley |
| 2011/0264229 A1 | 10/2011 | Donner |
| 2011/0295272 A1 | 12/2011 | Assell et al. |
| 2013/0030456 A1 | 1/2013 | Assell et al. |

FOREIGN PATENT DOCUMENTS

| | | |
|---|---|---|
| WO | 0234147 A1 | 5/2002 |
| WO | 2005039651 A2 | 5/2005 |
| WO | 2007016684 A2 | 2/2007 |
| WO | 2007142830 A2 | 12/2007 |
| WO | 2008021656 C2 | 2/2008 |
| WO | 2008060277 A2 | 5/2008 |
| WO | 2008103839 A2 | 8/2008 |
| WO | 2009029074 A1 | 3/2009 |
| WO | 2009143496 A1 | 11/2009 |
| WO | 2010017631 A9 | 2/2010 |
| WO | 2010065015 A1 | 6/2010 |
| WO | 2012015976 A1 | 2/2012 |

* cited by examiner

BONE SCREW

REFERENCE TO RELATED APPLICATION

This application claims priority to U.S. Provisional Application No. 61/495,212, which was filed on Jun. 9, 2011, the contents of which are incorporated herein by reference.

FIELD OF THE INVENTION

The invention relates generally to a device for joining together bones. More particularly, the invention relates to a bone screw.

BACKGROUND OF THE INVENTION

There are various times at which it is desired to hold bones within a human or animal body in a fixed position with respect to each other. One such situation where it is desired to hold bones together is when performing a sacroiliac fusion. Another situation where it is desirable to hold bones together is after a fracture.

In both of the preceding situations, a screw or other fixation device may be inserted into the two separate bone pieces. The screw thereby holds the bones in a stationary position until bone grows therebetween to thereby fuse the bone pieces together. Such bone growth thereby supplements the strength provided by the bone screw to prevent the bones from moving.

Various bone screws have been developed for use in conjunction with holding bones together. One such bone screw is disclosed in Ray et al., U.S. Pat. No. 4,961,740. The Ray bone screw has a threaded outer surface and an opening formed in a center portion thereof. The opening is adapted to receive bone growth inducing material. The Ray bone screw is particularly adapted for use in conjunction with maintaining adjacent vertebrae in a stationary position with respect to each other as part of a spinal fusion surgical procedure.

SUMMARY OF THE INVENTION

An embodiment of the invention is directed to a bone screw that includes a main body portion having a proximal end and a distal end. An external threaded surface and an internal threaded surface are formed on the main body portion. The external threaded surface intersects the internal threaded surface proximate a lower surface of the external threaded surface and a lower surface of the internal threaded surface. A plurality of bone growth apertures is defined on a surface of the main body portion where the external threaded surface and the internal threaded surface are not located. The bone growth apertures occupy between about 10 percent and about 60 percent of the surface of the main body portion.

Another embodiment of the invention is directed to a bone screw that includes a main body portion having a first threaded region on at least a portion of an outer surface thereof. The main body portion has a first end and a second end. A central bore is formed in the main body portion and extends along an axis of the main body portion. At least 3 side bores are formed in the main body portion. The side bores intersect the main body portion and the first threaded region.

Another embodiment of the invention is directed to a bone fixation kit that includes a bone screw and an insertion key. The bone screw includes a main body portion having a proximal end and a distal end. An external threaded surface and an internal threaded surface are formed on the main body portion.

The external threaded surface intersects the internal threaded surface proximate a lower surface of the external threaded surface and a lower surface of the internal threaded surface. A plurality of bone growth apertures is defined on a surface of the main body portion where the external threaded surface and the internal threaded surface are not located. The bone growth apertures compose between about 10 percent and about 60 percent of the surface of the main body portion. The insertion key is engageable with the internal threaded surface.

Still another embodiment of the invention is directed to a method of securing at least two bones to each other. An aperture is formed that extends between a first bone and a second bone. A bone screw is provided that includes a main body portion having a proximal end and a distal end. An external threaded surface and an internal threaded surface are formed on the main body portion.

The external threaded surface intersects the internal threaded surface proximate a lower surface of the external threaded surface and a lower surface of the internal threaded surface. A plurality of bone growth apertures is defined on a surface of the main body portion where the external threaded surface and the internal threaded surface are not located.

The bone growth apertures comprise between about 10 percent and about 60 percent of the surface of the main body portion. An insertion key is positioned at least partially in engagement with the internal threaded surface. The insertion key is rotated to cause the bone screw to be screwed into the first bone and the second bone.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION OF THE PREFERRED EMBODIMENTS

An embodiment of the invention is directed to a bone screw as illustrated at 10 in FIGS. 1-4. The bone screw 10 is adapted for use in a variety of applications in joining together bones within a human or animal body. One such suitable use for the bone screw 10 is for use in joining together the sacrum and the ilium in conjunction with a sacroiliac fusion surgical procedure.

The bone screw 10 has a generally elongated configuration with a substantially cylindrical outer surface. A length of the bone screw 10 may be selected based upon the type of surgical procedure in which the bone screw 10 in intended to be used. In certain embodiments, the bone screw 10 has a length of up to about 100 millimeters. In other embodiments, the bone screw 10 has a length of about 50 millimeters.

Similarly, an outer diameter of the bone screw 10 may be selected based upon the type of surgical procedure in which the bone screw 10 in intended to be used. In certain embodiments, the bone screw 10 may have a diameter of up to about 50 millimeters. In other embodiments, the outer diameter of the bone screw 10 is about 12.5 millimeters.

The bone screw 10 may include an external threaded surface 20 that extends over at least a portion of an outer surface thereof. The external threaded surface 20 enables the bone screw 10 to engage the bone through which the bone screw 10 is extended.

The external threaded surface 20 may be configured so that the external threaded surface 20 is tapered to a distal edge thereof. Forming the external threaded surface 20 with the tapered configuration enables the distal edge to cut into bone that is adjacent to the bone screw 10 as the bone screw 10 is screwed into the bone.

In certain embodiments, the thread 22 extends up to about 20 times around the bone screw 10. In other embodiments, the thread 22 extends between about 5 and 10 times around the bone screw 10.

The threads 22 should have sufficient depth so that the threads 22 are able to engage the bone to thereby prevent the bone screw 10 from sliding with respect to the bone after the bone screw 10 has been screwed into the bone. In certain embodiments, the depth of the threads 22 is between about 2 millimeters and about 5 millimeters.

The pitch of the threads 22 on the bone screw 10 may be selected to provide a reasonable rate at which the bone screw 10 may be screwed into the bone. In certain embodiments, the threads 22 may be oriented on the bone screw 10 at a pitch of up to about 5 millimeters. In other embodiments, the thread pitch may be about 2.5 millimeters.

A central bore 40 is formed in the bone screw 10. The central bore 40 may be oriented about a central bore axis that is substantially aligned with a central axis of the bone screw 10. The central bore 40 may extend substantially between a proximal end 26 and a distal end 28 of the bone screw 10.

In certain embodiments, the central bore 40 has a diameter of between about 3 millimeters and about 10 millimeters. In other embodiments, the central bore 40 has a diameter of about 5 millimeters.

In certain embodiments, the central bore 40 may have an inner diameter that is substantially consistent between the proximal end 26 and the distal end 28. In other embodiments, the inner diameter of the central bore 40 may vary at different locations of the bone screw 10. In one such embodiment, the inner diameter of the central bore 40 is greater proximate the proximal end 26 than proximate the distal end 28.

An internal threaded surface 38 is formed on at least a portion of the central bore 40. In certain embodiments, the internal threaded surface 38 extends substantially between the proximal end 26 and the distal end 28.

The external threaded surface 20 may engage the internal threaded surface 38 proximate lower surfaces of the external threaded surface 20 and the internal threaded surface 38.

Increasing the amount of times that the external threaded surface 20 and the internal threaded surface 38 intersect increases a strength of the bone screw 10. Similarly, increasing the width of the lower surfaces of the external threaded surface 20 and the internal threaded surface 38 increases a strength of the bone screw 10.

A plurality of bone growth apertures 58 are defined in the bone screw 10 where neither the external threaded surface 20 and the internal threaded surface 38 are located. Increasing the percentage of the bone screw 10 that is composed of the bone growth apertures 58 enhances the ability of bone to grow through the bone screw 10. However, increasing the percentage of the bone screw 10 composed of the bone growth apertures 58 decreases the strength of the bone screw 10.

In certain embodiments, the bone growth apertures 58 may compose between about 10 percent and about 60 percent of the bone screw 10. In other embodiments, the bone growth apertures 58 compose between about 20 percent and about 40 percent of the bone screw 10.

While it is possible for the internal threaded surface 38 and the external threaded surface 20 to each be formed with a similar pitch, in certain embodiments, the internal threaded surface 38 may have a pitch that is different than the pitch of the external threaded surface 20.

In certain embodiments, the internal threaded surface 38 has a pitch that is greater than a pitch of the external threaded surface 20. Forming the internal threaded surface 38 with a pitch that is greater than the pitch of the external threaded surface 20 may increase the points of contact between the internal threaded surface 38 and the external threaded surface 20. Such a configuration may enhance the strength of the bone screw 10.

Figure 1:
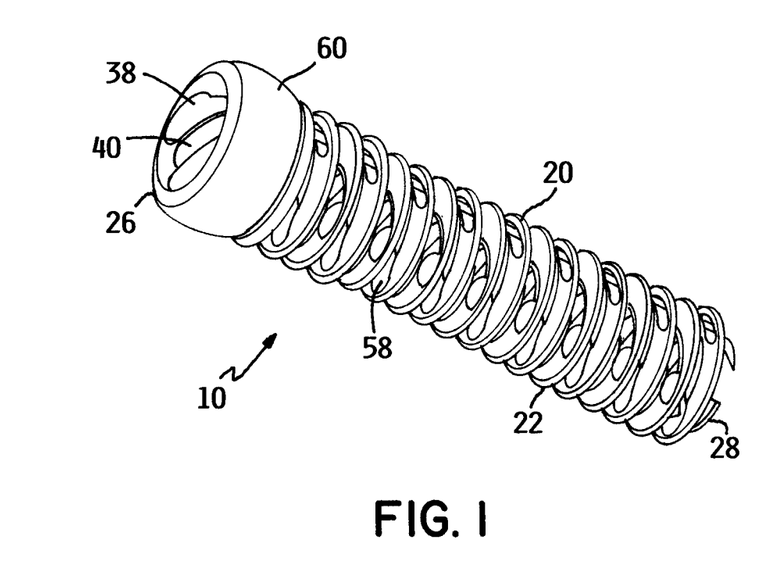
FIG. 1 is a perspective view of a bone screw according to an embodiment of the invention.
Figure 2:
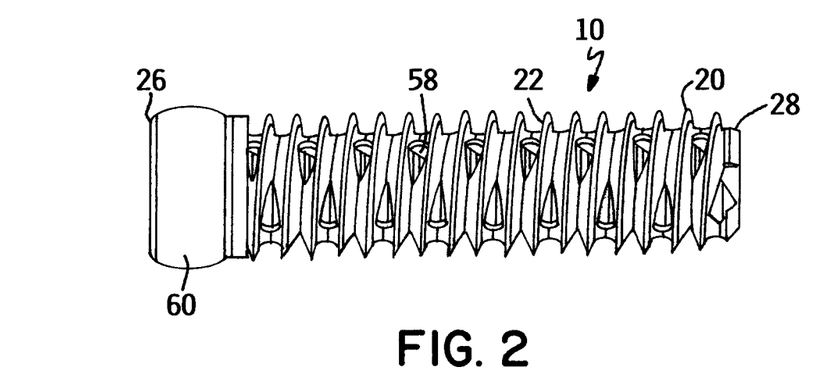
FIG. 2 is a side view of the bone screw of FIG. 1.
Figure 3:
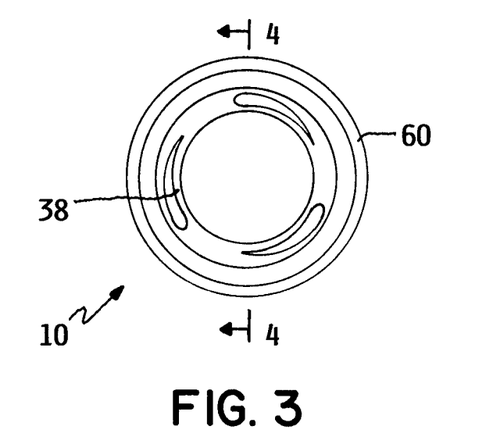
FIG. 3 is an end view of the bone screw of FIG. 1.
Figure 4:
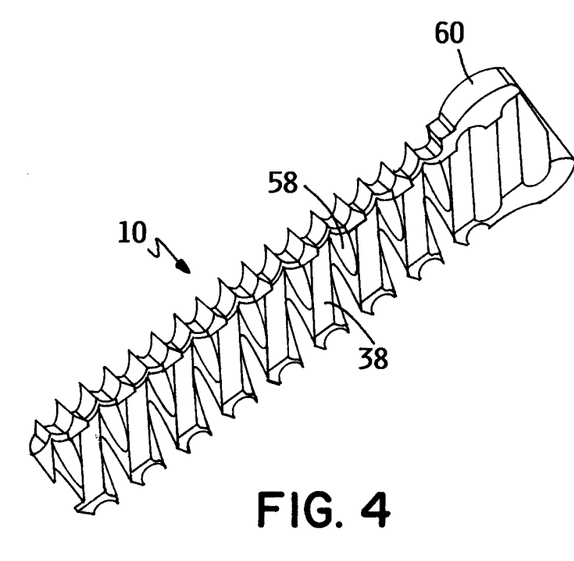
FIG. 4 is a sectional view of the bone screw taken along a line 4-4 in FIG. 3.

In certain embodiments, the internal threaded surface 38 may be formed with a pitch that enables there to be three thread starts proximate the proximal end 26 thereof, as illustrated in FIG. 3. The three thread starts may be spaced at an approximately equal distance from each other around the inner surface of the bone screw 10.

A distal edge of the internal threaded surface 38 may be substantially flat and side surfaces of the internal threaded surface 38 may be oriented generally transverse to the distal edge. Forming the internal threaded surface 38 with this configuration facilitates screwing an insertion device (not shown) into the bone screw 10.

The insertion device may have an external threaded surface on at least a portion thereof, which is shaped generally complementarily to the internal threaded surface 38. Once the insertion device is screwed into the central bore 40, continued rotation of the insertion device causes the bone screw 10 to be screwed into the bone.

Once the bone screw 10 is screwed a desired distance into the bone, the insertion device may be rotated in a direction that is opposite direction that was used to screw the bone screw 10 into the bone. This rotation causes the insertion device to be unscrewed with respect to the bone screw 10 until the insertion device may be separated from the bone screw 10.

The proximal end 26 of the bone screw 10 may include a head portion 60. The head portion 60 may extend over a relatively small portion of the length of the bone screw 10, as compared to the length of the bone screw 10 over which the external threaded surface 20 extends.

In certain embodiments, the head portion 60 may have a length of between about 5 millimeters and about 20 millimeters. In other embodiments, the head portion 60 may have a length of about 5 millimeters.

The head portion 60 may have a diameter that is greater than a diameter of the external threaded surface 20. Forming the head portion 60 with a diameter that is greater than a diameter of the external threaded surface 20 causes the bone screw 10 to resist being screwed into the bone once the bone screw 10 is inserted sufficiently into the bone so that the bone contacts the head portion 60.

In certain embodiments, the head portion 60 may have an outer diameter of between about 10 millimeters and about 20 millimeters. In other embodiments, the outer diameter of the head portion 60 is about 15 millimeters.

An outer surface of the head portion 60 may be substantially smooth to resist the potential of the head portion 60 snagging or otherwise engaging other objects as the bone screw 10 is screwed into the bone.

Because of the direction of the internal threaded surface 38, it is not possible to use the internal threaded surface 38 in conjunction with unscrewing the bone screw 10 from the bone. If it is envisioned that it may be necessary to unscrew the bone screw 10 from the bone, the head portion 60 may include a bone screw removal mechanism on at least a portion of a surface thereof.

In certain embodiments, the bone screw removal mechanism may include a non-circular region on the head portion 60. The non-circular region may be substantially flat or may include a recess. This non-circular region may be engaged by a removal device (not shown) that extends over at least a portion of head portion 60. Once the removal device engages the head portion 60, rotation of the removal device causes the bone screw 10 to be unscrewed from the bone.

One suitable technique that may be used for fabricating the bone screw 10 is to machine a solid piece of metal into a desired shape. This technique lends itself to forming a cylindrical bore through the bone screw 10 such as using a drill and then using a tap to form the internal threaded surface 38. It is also possible to fabricate the bone screw 10 from a variety of other materials. Such other materials should be biocompatible. Examples of such other materials include polymeric materials.

Bone growth through the bone screw 10 may also be increased by placing a bone-growth inducing material in the central bore 40. Examples of bone-growth inducing materials include bone chips, bone substitutes and bone activating material. The bone-growth inducing material may be placed into the central bore 40 after the bone screw 10 has been screwed into the bone.

A retaining device may be placed adjacent to at least one of the proximal end 26 and the distal end 28 of the bone screw 10 to retain the bone-growth inducing material within the central bore 40. An example of one suitable retaining device is a mesh.

Another embodiment of the invention is directed to a bone screw as illustrated at 110 in FIGS. 5-8. The bone screw 110 is adapted for use in a variety of applications in joining together bones within a human or animal body. One such suitable use for the bone screw 110 is for use in joining together the sacrum and the ilium in conjunction with a sacroiliac fusion surgical procedure.

The bone screw 110 has a generally elongated configuration with a substantially cylindrical outer surface. A length of the bone screw 110 may be selected based upon the type of surgical procedure in which the bone screw 110 in intended to be used. In certain embodiments, the bone screw 110 has a length of up to about 100 millimeters. In other embodiments, the bone screw 110 has a length of about 50 millimeters.

Similarly, a diameter of the bone screw 110 may be selected based upon the type of surgical procedure in which the bone screw 110 in intended to be used. In certain embodiments, the bone screw 110 may have a diameter of up to about 50 millimeters. In other embodiments, the bone screw 110 has a diameter of about 12.5 millimeters.

The bone screw 110 may include an external threaded surface 120 that extends over at least a portion of an outer surface thereof. The external threaded surface 120 enables the bone screw 110 to engage the bone through which the bone screw 110 is extended.

In certain embodiments, the thread 122 extends up to about 20 times around the bone screw 110. In other embodiments, the thread 122 extends between about 5 and 10 times around the bone screw 110.

The threads 122 should have sufficient depth so that the threads 122 are able to engage the bone to thereby prevent the bone screw 110 from sliding with respect to the bone after the bone screw 110 has been screwed into the bone. In certain embodiments, the depth of the threads 122 is between about 2 millimeters and about 5 millimeters.

The pitch of the threads 122 on the bone screw 110 may be selected to provide a reasonable rate at which the bone screw 110 may be screwed into the bone. In certain embodiments, the threads 122 may be oriented on the bone screw 110 at a pitch of up to about 5 millimeters. In other embodiments, the thread pitch may be about 2.5 millimeters.

An interior of the bone screw 110 may serve at least two functions. The first function is to provide a recess into which a portion of a bone screw insertion key may be inserted for screwing the bone screw 110 into the bone. The second function is to provide a sufficient amount of open space through which bone may grow.

The two preceding functions must be balanced so that the bone screw 110 has sufficient strength to be screwed into the bones and the bone screw 110 has sufficient strength to maintain the bones in a stationary position during the early stage of the bone growth process while the bone screw 110 has sufficiently large open areas for bone growth.

One suitable technique that may be used for fabricating the bone screw 110 is to machine a solid piece of metal into a desired shape. This technique lends itself to forming cylindrical bores through the bone screw 110 such as using a drill. It is also possible to fabricate the bone screw 110 from a variety of other materials. Such other materials should be biocompatible. Examples of such other materials include polymeric materials.

In one such configuration, there is a central bore 140 formed therein. The central bore 140 may be oriented about a central bore axis that is substantially aligned with a central axis of the bone screw 110.

In certain embodiments, the central bore 140 has a diameter of between about 3 millimeters and about 110 millimeters. In other embodiments, the central bore 140 has a diameter of about 5 millimeters.

To increase the regions in the bone screw 110 where bone can grow, it may be possible to form at least one side bore 142 that is oriented proximate an edge of the central bore 140. In certain embodiments, there are between about 4 and 10 side bores 142 placed around the central bore 140. In other embodiments, there are about 6 side bores 142 placed around the central bore 140.

In certain embodiments, the side bores 142 have a diameter of between about 0.5 millimeters and about 5 millimeters. In other embodiments, the side bores 142 have a diameter of between about 1 millimeter and about 2 millimeters.

The side bores 142 may be positioned to intersect the central bore 140. The side bores 142 thereby increase the area encompassed by the central bore 140. The side bores 142 may also be positioned to intersect the threads 122 proximate the grooves defined between adjacent threads 122. The side bores 142 may have a combined area that is between about 30 and 60 percent of the area of the central bore 140.

In certain embodiments, the side bores 142 intersect more than about 30 percent of an outer edge of the central bore 140. In other embodiments, the side bores 142 intersect more than about 50 percent of the outer edge of the central bore 140.

The side bores 142 and the central bore 140 thereby define a plurality of elongated members 144 that extend between the first end and the second end of the bone screw 110. These elongated members 144 engage the lower surfaces of the threads 122 to thereby maintain the threads 122 in a stationary position with respect to each other.

The elongated members 144 may have a generally trapezoidal shape with a profile that is substantially consistent along the length of the bone screw 110. This generally trapezoidal shape is a function of the shape of the central bore 140, the side bores 142 and the grooves between each of the threads 122.

While positioning the side bores 142 so that the side bores 142 intersect the threads 122 increases the space for the bone to grow around the bone screw 110, forming the side bores 142 in such a configuration could weaken the threads 122 and thereby lead to breakage of the threads 122.

To ensure that the bone screw 110 retains sufficient strength, the side bores 142 should extend into the threads 122 less than about 50% of the height of the threads 22. In other embodiments, the side bores 142 extend into the threads 122 to a distance of between about 20% and 30% of the height of the threads 122.

Since the height of the thread 122 that is intersected by the side bore 142 affects a strength of the bone screw 110 similar to the number of side bores 142 formed in the bone screw 110, these elements should be balanced to ensure that the bone screw 110 has sufficient strength to not deform while being screwed into the patient's bone as well as after being inserted into the patient before the bone has the opportunity to grow around and through the bone screw 110.

In certain embodiments, the outer edge of the threads 122 may have a consistent diameter along a significant portion of the length of the bone screw 110. Proximate at least one of the ends of the bone screw 110, the outer edge of the threads 122 may have a slightly narrower diameter to enhance the ability to start screwing the bone screw 110 into the patient's bone.

The bone screw 110 is illustrated as being symmetrical with two similarly shaped threaded regions 120 proximate opposite ends thereof. Such a configuration is suited for a variety of applications. One such suitable application for this configuration of the bone screw 110 is for sacroiliac fusion.

It is also possible to form the bone screw 110 with different configurations as well as different numbers of threaded regions 120 so that the bone screw 110 may be suited for different application. It is also possible to position the threaded regions 120 on the bone screw 110 in an asymmetrical configuration.

Figure 5:
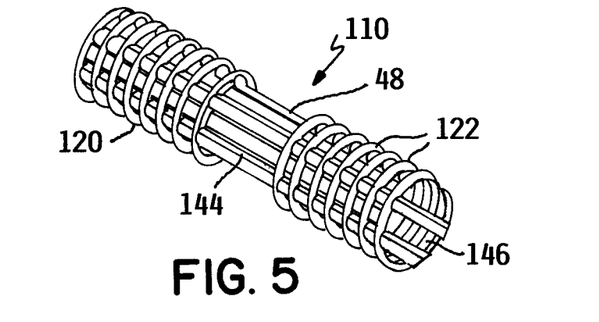
FIG. 5 is a perspective view of a bone screw according to another embodiment of the invention.
Figure 6:
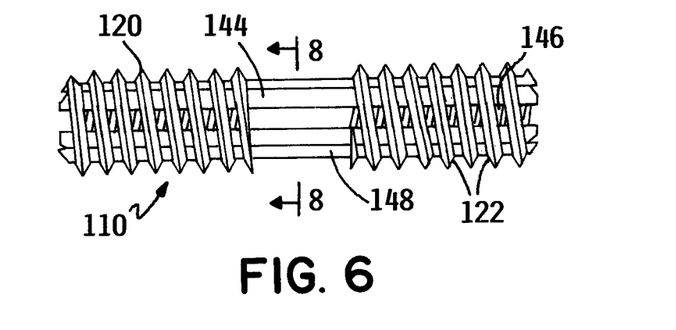
FIG. 6 is a side view of the bone screw of FIG. 5.
Figure 7:
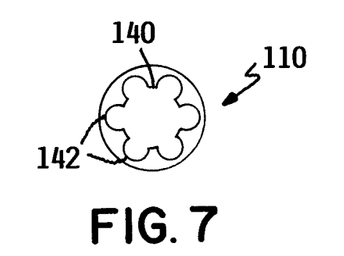
FIG. 7 is an end view of the bone screw of FIG. 5.
Figure 8:
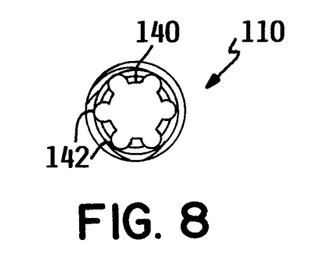
FIG. 8 is a sectional view of the bone screw taken along a line 8-8 in FIG. 6.

The bone screw 110 may include a region 148 that does not include any threads 122, as illustrated in FIGS. 5-6. This non-threaded region 148 may be positioned proximate an intermediate location on the bone screw 110. The position on the non-threaded region 148 on the bone screw 110 may correspond to a position of the interface between the first bone and the second bone after the bone screw 110 has been inserted.

An inventive aspect of the bone screw 110 relates to a process of holding at least two bones together so that the bones do not move with respect to each other such as when a single bone has been fractured into at least two pieces.

While the bone screw 110 holds the at least two bones together, it is typically desirable to supplement the strength of the bone screw by encouraging bone growth between the at least two bone pieces. Such bone growth causes the at least two bones to fuse together.

The more area that is encompassed by the bone growth, the stronger the fusion between the at least two bones. Accordingly, the more surface area of the bone screw 110 that is encompassed by the bone growth apertures 146, the stronger the fusion between the at least two bones.

The bone growth apertures 146 extend from the outer surface of the bone screw 110 to the central bore 140. The bone growth apertures 146 may have a profile that is generally in the shape of a parallelogram that is defined on two sides by adjacent threads 122 and on two sides by the elongated members 144.

In certain embodiments, the bone growth apertures 146 occupy between about 20 percent and about 60 percent of the outer surface of the bone screw 110. In other embodiments, the bone growth apertures 146 occupy between about 30 percent and about 50 percent of the outer surface of the bone screw 110.

However, increasing the percentage of the surface area of the bone screw 110 encompassed by the bone growth apertures 146 can negatively impact the structural strength of the bone screw 110. Such decrease in the strength of the bone screw 110 may be offset by the support provided to the bone screw 110 by the insertion key that is inserted into the bone screw 110 prior to screwing the bone screw 110 into the at least two bones.

Bone growth through the bone screw 110 may also be increased by placing a bone-growth inducing material in the central bore 140. Examples of bone-growth inducing materials include bone chips, bone substitutes and bone activating material. The bone-growth inducing material may be placed into the central bore 140 after the bone screw 110 has been screwed into the bone.

A retaining device may be placed adjacent to at least one of the proximal end and the distal end of the bone screw 110 to retain the bone-growth inducing material within the central bore 140. An example of one suitable retaining device is a mesh.

The insertion key may include a handle portion and a key portion that extends from the handle portion. The handle portion is suitable for being gripped by a person using the insertion key. In one such configuration, the handle portion may be configured similar to a handle on a conventional screwdriver. In other embodiments, the handle portion may be oriented at least partially transverse to the key portion. This transverse orientation may increase the torque that may be applied to the bone screw 110 using the insertion key.

The key portion is adapted for being at least partially extended into at least one of the central bore 140 and the side bores 142. In certain embodiments, the key portion has a profile that generally conforms to a profile of the central bore 140. Contact between the key portion and the central bore 140 thereby causes the key portion to enhance the strength of the bone screw 110, which reduces the potential of the bone screw 110 being deformed as the bone screw 110 is being screwed into the at least one bone.

The key portion may have a hexagonal profile when there are 6 side bores 142 formed in the bone screw 110. The sides of the hexagon may be positioned adjacent to the surfaces of the bone screw 110 that are between each of the side bores 142. The corners of the hexagon may at least partially extend into the side bores 142. This configuration substantially prevents the insertion key from rotating with respect to the bone screw 110.

In certain embodiments, the key portion has a length that is at least as long as the length of the bone screw 110. If the key portion has a length that is greater than a length of the bone screw 110, a stop may be provided on the key portion to prevent a distal end of the key portion from being extended beyond a distal end of the bone screw 110.

In another embodiment, the key portion includes a plurality of extensions that each extend from the handle portion. The extensions may have an outer profile that at least partially conforms to a surface of the side bores 142. The extensions are mounted in a spaced-apart configuration so that one of the extensions may be extended into each of the side bores 142.

Another technique for fabricating the bone screw 110 is to form the first threaded region and the second threaded region that each only include a thread having a desired depth, pitch and number of revolutions.

Thereafter, at least one elongated member is positioned adjacent to the lower surface of the threads and being oriented parallel to but offset from a central axis of the first threaded region and the second threaded region. The elongated member is then attached to at least a portion of the threads.

Increasing the number of elongated members increases the strength of the bone screw. In certain embodiments, there are 6 elongated members positioned in a spaced-apart orientation around the inner surface of the threads 122. The configuration may thereby be similar to the configuration illustrated in FIGS. 5-8 where the elongated members 144 are defined by the central bore 140 and the plurality of side bores 142 formed in the main body portion.

A variety of techniques may be used for attaching the elongated members to the threads 122. An example of one suitable technique that may be used for attaching the elongated members to the threads 122 is welding.

Rotation of the tool causes the bone screw 110 to rotate with respect to the bone such that the bone screw 110 can be screwed into the bone. This process is continued until the bone screw 110 is inserted to a desired extent into the bone. In certain embodiments, once the bone screw 110 is fully inserted into the bone, the proximal and distal ends of the bone screw 110 are recessed within the bone.

In certain embodiments, prior to insertion of the bone screw 110 into the bone, an aperture may be formed in the bone. The aperture may have a diameter that is greater than a diameter of the bone screw 110 proximate the grooves and that is less than a diameter of the bone screw 110 proximate the upper end of the lands. One suitable technique for forming the aperture in the bone is a drill bit.

Figure 9:
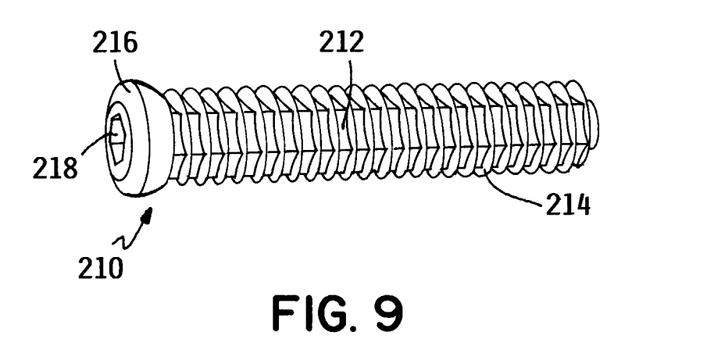
FIG. 9 is a perspective view of a bone screw according to another embodiment of the invention.

In another embodiment of the invention, which is illustrated in FIG. 9, the bone screw 210 has a non-circular core portion 212 and a thread portion 214 extending therefrom. The core portion 212 may be formed with a variety of different shapes using the concepts of the invention. An example of several suitable shapes for the non-circular core portion 212 is a triangle, square, pentagon, hexagon, heptagon and octagon.

One difference between the bone screw having a circular core and a non-circular core is that a distance between an upper edge of the thread and a lower edge of the thread is generally consistent for the bone screw with the circular core while this distance varies with the bone screw having the non-circular core.

The non-circular core portion 212 may reduce the potential of the bone screw 210 rotating with respect to the adjacent bone after insertion because bone would grow into the flat regions defined by the non-circular core portion 212.

The thread portion 214 may include a tapered configuration in which a width of the thread portion 214 is greater proximate the intersection of the thread portion 214 and the core portion 212 than proximate an end of the thread portion 214 that is furthest away from the core portion 212. Forming the thread portion 214 with this configuration enhances the ability of the thread portion 214 to cut into the bone as the bone screw 210 is screwed into the bone.

The thread portion 214 may be formed with a height that is sufficiently great so that the thread portion 214 cuts into the bone to reduce the potential of the bone screw 210 becoming disengaged from the bone such as by rotating out or sliding out. On the other hand, the height of the thread portion 214 should not be too large because that would increase the difficulty associated with screwing the bone screw 210 into the bone.

The thread portion 214 should be formed with a pitch that is relatively flat such that there is either one or two starts. While using such a configuration may increase the number of rotations needed to insert the bone screw 210 into the bone, this configuration would reduce the potential of the bone screw 210 rotating in a reverse direction after insertion to cause the bone screw 210 to back out of the bone.

A distal end of the bone screw 210 may be formed with a taper to facilitate alignment of the bone screw 210 with an aperture formed in the bone. In certain configurations, it is not necessary for the bone screw to start an aperture in the bone because in many situations, the aperture is drilled prior to the process of screwing the bone screw 210 into the bone.

The bone screw 210 may have a head portion 216 at a proximal end thereof. The head portion 216 may have a diameter that is greater than a diameter of at least one of the core portion 212 and the thread portion 214. The head portion 216 may thereby assist with preventing over-insertion of the bone screw 210 by engaging the bone that is adjacent to the bone screw 210 during the insertion process. In certain embodiments, an outer surface of the head portion 216 may be relatively smooth.

The bone screw 210 may include a mechanism that facilitates rotation of the bone screw 210 during the insertion process. An example of one such mechanism that may be used is a recess 218 formed in the proximal end of the bone screw 210 such as being formed in the head portion 216.

In one such embodiment, the recess 218 has a non-circular configuration. For example, the recess 218 may have a hexagonal shape. The recess is adapted for engagement by an insertion tool (not shown) that is used to rotate the bone screw 210 during the insertion process.

The bone screw 210 may be fabricated from a variety of materials using the concepts of the invention. In certain embodiments, the thread portion 214 is integrally formed with the core portion portion 212 and is formed from the same material as the core portion 212. In other embodiments, the thread portion 214 is formed separate from the core portion 212 and then attached to the core portion 212. It is also possible that the thread portion 214 may be formed from a different material than the core portion 212.

Examples of suitable materials that may be used in fabricating at least one of the core portion 212 and the thread portion 214 include titanium, titanium alloy, ceramics, polymers and combinations thereof.

The bone screw 210 should facilitate forming a strong bond between the bone screw 210 and the adjacent bone. An outer surface of at least one of the core portion 212 and the thread portion 214 may be covered with a fusion-promoting material. Examples of suitable fusion-promoting materials are allograft bone, cortical bone, tricalcium phosphates, hydroxyapatite, BIOCRYL™ hydroxyapatite, bioglass, polymer composites, bone-derived substances, demineralized bone matrix, mineralizing proteins, ossifying proteins, bone morphogenetic proteins, genes coding for the production of bone and combinations thereof.

Alternatively or additionally, an outer surface of at least one of the core portion 212 and the thread portion 214 may be textured to enhance a bond between the bone screw 210 and the adjacent bone. An example of one suitable text involves forming a plurality of recesses in the outer surface of at least one of the core portion 212 and the thread portion 214. The plurality of recesses may have a relatively small diameter and may cover a relatively large proportion of the outer surface of the core portion 212 and the thread portion 214.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A bone screw comprising a main body portion having a proximal end and a distal end, wherein an external threaded surface and an internal threaded surface are formed on the main body portion, wherein the external threaded surface intersects the internal threaded surface proximate a lower surface of the external threaded surface and a lower surface of the internal threaded surface, wherein a plurality of bone growth apertures is defined on a surface of the main body portion where the external threaded surface and the internal threaded surface are not located and wherein the bone growth apertures comprise between about 10 percent and about 60 percent of the surface of the main body portion, and further comprising a head portion attached to the main body portion proximate the proximal end, wherein the head portion has an outer diameter that is greater than an outer diameter of the external threaded portion.

2. The bone screw of claim 1, wherein the external threaded surface has a pitch that is different than a pitch of the internal threaded surface.

3. The bone screw of claim 1, wherein the external threaded surface has one thread start and wherein the internal threaded surface has at least two thread starts.

4. The bone screw of claim 1, wherein the external threaded surface and the internal threaded surface each extend substantially between the proximal end and the distal end.

5. The bone screw of claim 1, wherein the head portion further comprises a non-circular region.

6. The bone screw of claim 1, wherein the external threaded surface has a pointed distal edge and wherein the internal threaded surface has a substantially flat distal edge.

7. The bone screw of claim 1, wherein the main body portion has a central bore that extends therethrough, wherein the central bore extends between the proximal end and the distal end and wherein an inner diameter of the central bore is substantially the same between the proximal end and the distal end.

* * * * *